(12) United States Patent
Griffin et al.

(10) Patent No.: US 7,351,402 B2
(45) Date of Patent: Apr. 1, 2008

(54) POLARIZING AGENTS FOR DYNAMIC NUCLEAR POLARIZATION

(75) Inventors: Robert G. Griffin, Newton, MA (US); Kan-Nian Hu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 401 days.

(21) Appl. No.: 10/920,900

(22) Filed: Aug. 18, 2004

(65) Prior Publication Data

US 2005/0107696 A1 May 19, 2005

Related U.S. Application Data

(60) Provisional application No. 60/496,792, filed on Aug. 21, 2003.

(51) Int. Cl.
*A61K 40/00* (2006.01)
*A61B 5/055* (2006.01)
*A61B 5/05* (2006.01)
*G01N 24/00* (2006.01)

(52) U.S. Cl. .................... 424/9.33; 424/9.3; 600/420; 600/431; 436/173

(58) Field of Classification Search ............... 424/9.33, 424/9.3; 600/431, 410; 436/173; 546/184, 546/245, 248; 514/315; 900/933
See application file for complete search history.

(56) References Cited

U.S. PATENT DOCUMENTS

| | | | | |
|---|---|---|---|---|
| 5,435,991 | A | * | 7/1995 | Golman et al. ............. 424/9.33 |
| 6,311,086 | B1 | * | 10/2001 | Ardenkjaer-Larsen et al. ... 600/420 |
| 7,102,354 | B2 | * | 9/2006 | Ardenkjaer-Larsen et al. ... 324/321 |
| 2002/0058869 | A1 | * | 5/2002 | Axelsson et al. ........... 600/423 |
| 2004/0039281 | A1 | | 2/2004 | Cook ......................... 600/420 |

FOREIGN PATENT DOCUMENTS

WO     WO 96/39367    * 12/1996

OTHER PUBLICATIONS

Kirste et al., J. Am. Chem. Soc., 1982, 104, p. 3850-3858.*
Bagryanskaya, E. et al., Russian Chemical Reviews, 2000, 69, p. 925-945.*
International Search Report (PCT/US04/26968).
Bajaj et al., "Dynamic Nuclear Polarization at 9 T Using a Novel 250 GHz Gyrotron Microwave Source," J. Magn. Resonance 160, 85-90, 2003.
Farrar et al., "Mechanism of Dynamic Nuclear Polarization in High Magnetic Fields," Journal of Chemical Physics, 114(11): 4922-4933, 2001.
Gagnaire, et al., "Regulation by Potassium Ions of Spin Exchange and Dipolar Splitting in Biradical. A Simple Allosteric System," Tetrahedron Letters, 30(47):6507-6510, 1989.
Henstra, "High Dynamic Nuclear Polarization at Room Temperature," Chemical Physics Letters, 165(1):6-10, 1990.
Hu et al., "Dynamic Nuclear Polarization with Biradicals" J. Am. Chem. Soc. 126, 10844-10845, 2004.
Luckhurst, G., "Biradicals as Spin Probes" in *Spin Labeling Theory and Applications*, pp. 133-181, L. Berliner Editor, Academic Press (1976).
Rosay et al., "Two-dimensional $^{13}C$—$^{13}C$ Correlation Spectroscopy with Magic Angle Spinning and Dynamic Nuclear Polarization," J. Amer. Chem. Soc., 124(13):3214-3215, 2002.
Rosay et al., "High Frequency Dynamic Nuclear Polarization in MAS Spectra of Membrane and Soluble Proteins," J. Amer. Chem. Soc. 125, 13626-27 (2003).
Turro et al., "An Electron Spin Polarization Study of the Interaction of Photoexcited Triplet Molecules with Mono-and Polynitroxyl Stable Free Radicals," J. Phys. Chem. 97:1138-1146, 1993.
van den Heuvel, "Transient Oscillations in Pulsed Dynamic Nuclear Polarization," Chemical Physics Letters, 188(3-4):194-200, 1992.

* cited by examiner

*Primary Examiner*—Michael G. Hartley
*Assistant Examiner*—Leah Schlientz
(74) *Attorney, Agent, or Firm*—Choate, Hall & Stewart, LLP

(57) ABSTRACT

We describe polarizing agents for use in enhancing NMR and MRI signals via dynamic nuclear polarization (DNP). The polarizing agents include two or more paramagnetic centers, preferably two paramagnetic centers. In a preferred embodiment, the polarizing agent comprises two nitroxide radicals tethered by a polyethylene glycol chain of variable length. Signal enhancements of up to 175 have been achieved in comparison with factors of ~45 at similar concentrations of monomeric radical such as TEMPO.

20 Claims, 6 Drawing Sheets

Trityl-TEMPO Biradical

POLARIZING AGENTS FOR DYNAMIC NUCLEAR POLARIZATION

PRIORITY INFORMATION

This application claims priority to U.S. Ser. No. 60/496,792 filed Aug. 21, 2003 the entire contents of which are hereby incorporated by reference.

GOVERNMENT SUPPORT

This invention was made with government support under Grant No. 3-R01-GM38352-14S1, awarded by NIH. The government has certain rights in the invention.

BACKGROUND OF THE INVENTION

The present invention relates to polarizing agents for use in enhancing nuclear magnetic resonance (NMR) and magnetic resonance imaging (MRI) signals via dynamic nuclear polarization (DNP) and, more particularly, to such agents that include two or more paramagnetic centers.

For about 50 years it has been known that it is possible to enhance the intensities of NMR signals by increasing the nuclear spin polarization with DNP. In this method, paramagnetic centers are introduced into a sample in a magnetic field and the large electron spin polarization of these centers is converted to nuclear spin polarization of nuclei within the sample via microwave irradiation. In this context, it is customary to utilize radicals such as the nitroxide 2,2,6,6, tetramethylpiperadine-1-oxyl (TEMPO), metal centers like $Cr^{5+}$, or other monomeric paramagnetic centers. See, for example, Farrar et al., "Mechanism of Dynamic Nuclear Polarization in High Magnetic Fields," Journal of Chemical Physics, 114(11): 4922-4933, 2001. It is also known that short-lived photo-excited triplet states can be used as polarizing agents in DNP experiments. See, Henstra, "High Dynamic Nuclear Polarization at Room Temperature," Chemical Physics Letters, 165(1):6-10, 1990; and van den Heuvel, "Transient Oscillations in Pulsed Dynamic Nuclear Polarization," Chemical Physics Letters, 188(34):194-200, 1992.

SUMMARY OF THE INVENTION

In one aspect of the invention, the polarizing agent is a molecule that includes two or more unpaired electrons or paramagnetic centers. The chemical environment of the two or more paramagnetic centers may be similar or different, e.g., the paramagnetic centers may have either similar or different isotropic g-values and/or g-anisotropies.

When there are two unpaired electrons in the molecule, the polarizing agent is a ground state triplet molecule, e.g., a stable biradical molecule prepared by tethering two radical molecules via a linker which may have a variety of chemical compositions, structures and lengths chosen to optimize the efficiency as a polarizing agent. For example, specific linkers may be selected to increase the water solubility or reduce the flexibility of the polarizing agent. The length and structure of the linker may be adjusted so that the paramagnetic centers within the polarizing agent are separated by a distance that yields a dipolar coupling and a relative orientation of the g-tensors of the radicals that leads to optimal DNP.

In addition, the two tethered molecules that host the unpaired electrons may be identical or different in their chemical structure. When the two tethered radical molecules have the same structure and they have identical isotropic g-values and g-anisotropies, then it is preferred that the breadth of their EPR spectra be greater than the nuclear Larmor frequency of the nuclei that are to be polarized. When the two tethered radical molecules have different structures and different isotropic g-values and g-anisotropies, then it is preferable that the maxima in spectral intensity of the EPR spectra of the two paramagnetic centers be approximately separated by the nuclear Larmor frequency of the nuclei that are to be polarized. These two varieties of biradicals will support the thermal mixing or cross effect mechanism of DNP.

It will be appreciated that a variety of radicals may be tethered to form a stable biradical. Exemplary radicals that may be tethered are nitroxide radicals, such as TEMPO and proxyl. Without limitation, a suitable linker such as a polyethylene glycol chain of variable length may tether TEMPO radicals. A preferred polyethylene glycol chain is —$(CH_2-CH_2O)_n$— wherein n is 2, 3, or 4. In another embodiment, a trityl radical and a nitroxide radical such as TEMPO may be tethered to produce a suitable polarizing agent. Alternatively, the two radicals could be attached as spin labels on a molecular scaffold, e.g., a protein. Polarizing agents that include more than two paramagnetic centers may be prepared by tethering more than two radicals.

In another aspect, the invention provides a method of enhancing NMR signals of a sample via dynamic nuclear polarization by adding the polarizing agent to the sample, the polarizing agent comprising two or more paramagnetic centers, preferably two paramagnetic centers. The sample is then irradiated with high frequency microwaves and the nuclear spin polarization is enhanced. Another application of the invention involves enhancing MRI signals with DNP using the polarizing agent. The polarizing agent comprising two or more paramagnetic centers is added to a solution and the sample is polarized by irradiating with microwaves. In some cases this is accomplished at low temperature, for example, less than about 150 K, more preferably less than about 110 K, most preferably less than about 90 K. When the objective is to enhance MRI signals it is preferred that the sample being polarized include an imaging agent with a long nuclear longitudinal spin relaxation time constant ($T_1$). This will ensure that enhanced nuclear polarization within the imaging agent is maintained for a sufficient length of time for transfer into an organism of interest (e.g., a patient) and subsequent imaging.

BRIEF DESCRIPTION OF THE DRAWING

FIG. 1a shows the EPR spectrum of TEMPO, the positions of two electrons ($e_1$ and $e_2$) in the spectrum, and the irradiation of the powder pattern. FIG. 1b shows how the spin flips of two electrons ($e_1$ and $e_2$) separated by the nuclear Larmor frequency leads to polarization of the nuclear spin (n).

FIG. 5 is a plot of a series of DNP enhanced magic angle spinning spectra of $^{13}$C-urea. The figure also includes the pulse sequence that was used to obtain the spectra as an inset. The different spectra were obtained with increasing periods of microwave irradiation (from 0 to 15 seconds). The lower spectra were obtained with microwaves off and the upper spectra were obtained with microwaves on.

DESCRIPTION OF CERTAIN PREFERRED EMBODIMENTS OF THE INVENTION

First, we briefly summarize some of the theory on which the present invention is based. There are three common mechanisms employed in dynamic nuclear polarization (DNP) experiments—the Overhauser effect, the solid effect, and thermal mixing—and each is applicable in different experimental circumstances. When the sample is an insulating solid and the breadth of the EPR spectrum, δ, is greater than the nuclear Larmor frequency $\omega_n/2\pi$, then the thermal mixing/cross effect (TM/CE) mechanism is known to have optimal efficiency and dominates the polarization process. Thus, when nitroxide radicals, e.g., 2,2,6,6,tetramethylpiperidine-1-oxyl (TEMPO) are used as polarizing agents, the TM/CE mechanism provides the largest enhancements of the nuclear spin polarization.

Figure 1A:
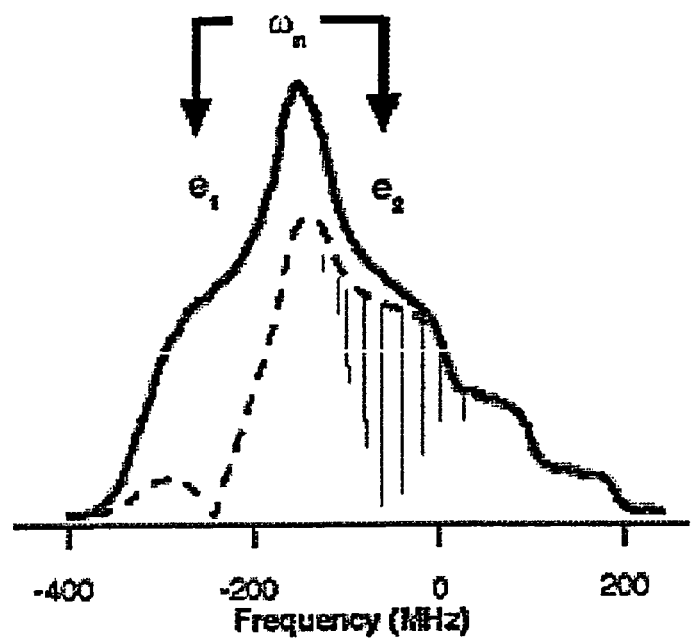
FIGS. 1a and 1b illustrate the thermal mixing/cross effect mechanism of DNP.
Figure 1B:

Without wishing to be bound to any particular theory, the current theoretical understanding of TM/CE-DNP by the inventors herein is that the polarization agents function via a three spin process involving two electrons and a nuclear spin. When the resonance frequency of the two electrons is separated by the nuclear Larmor frequency, the two electron spins can undergo mutual spin flips and the difference frequency, which matches the nuclear Larmor frequency, results in a nuclear spin flip and increased nuclear polarization. This is illustrated in FIGS. 1a and 1b.

The inventors herein have further recognized that the polarization transfer efficiency is governed by the size of the electron-electron dipolar interaction between the two electron spins and hence, that the efficiency of the TM/CE process is enhanced by increasing that coupling. The desire to increase the electron-electron dipolar interaction led the inventors to the concept disclosed and claimed herein of increasing the electron-electron dipole coupling, and therefore the efficiency of the DNP polarizing agent, by providing a polarizing agent that includes two or more physically connected paramagnetic centers, e.g., by tethering two radicals to form a biradical. It is contemplated that more than two radicals may be tethered. In order to illustrate this aspect of the invention we have prepared a series of exemplary biradicals comprising two TEMPO molecules tethered by a polyethylene glycol chain of variable length [(—CH$_2$—CH$_2$O)$_n$—, n=2, 3, or 4]. We note that as the polyethylene glycol chain length is decreased, the electron-electron dipole coupling increases resulting in increased signal enhancements in DNP experiments described below (see Example 1). Specifically, we have obtained $^{13}$C NMR enhancements of approximately 175, 110 and 80 with two TEMPO molecules tethered by a polyethylene glycol chain with n=2, 3, and 4, respectively. In comparison, an enhancement of 45 was obtained with the equivalent concentration of monomeric TEMPO. All experiments were performed at approximately 90 K.

In addition to producing larger enhancements, the use of a biradical has two further advantages. First, because of the larger electron-electron dipolar couplings, the concentration of the biradical required to achieve a given enhancement can be reduced relative to that of a monoradical such as TEMPO. For example, we obtain an enhancement of ~50 with 40 mM TEMPO but with the biradical we can obtain the same enhancement at a concentration of ~10 mM electrons or 5 mM of biradical. Since the concentration of electrons in the sample is lower by a factor of four, the corresponding electron-nuclear dipolar broadening is reduced by a factor of ~4. Second, since the electron-electron dipolar coupling is larger, the rate of polarization build up is faster.

Figure 2:
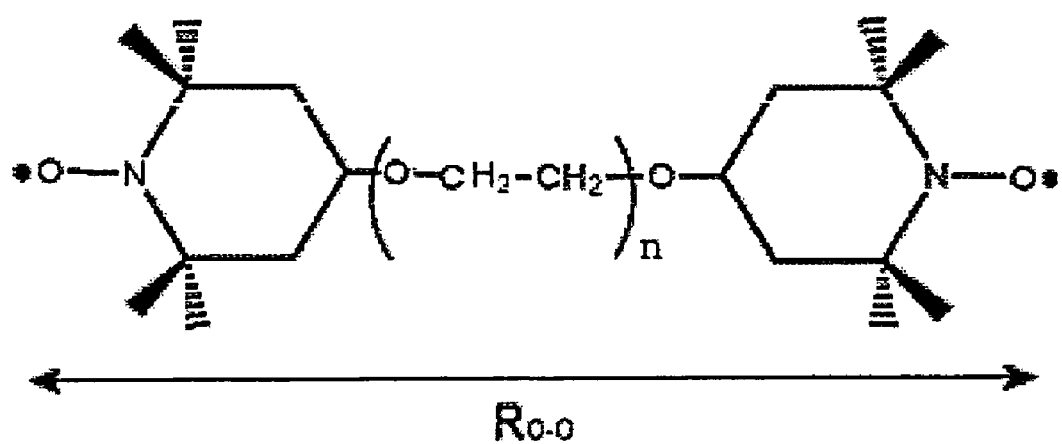
FIG. 2 is a schematic of a polarizing agent of one embodiment of the invention that includes two tethered radicals. The two radicals are the same (e.g., two nitroxide radicals) and are separated by a distance $R_{O-O}$. The width of the EPR spectrum of the polarizing agent is illustrated in FIG. 1a and is larger than the nuclear Larmor frequency of the nuclei that are to be polarized ($\omega_n/2\pi = v_n$).
Figure 3A:
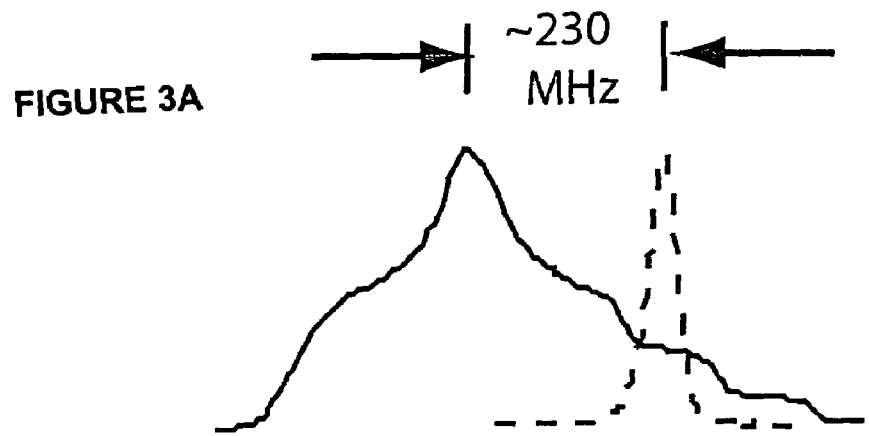
FIG. 3a is a schematic representation of an EPR spectrum of another embodiment of a polarizing agent that includes two tethered radicals. The two tethered radicals are different (e.g., a nitroxide radical and trityl) and the figure shows that the separation between the maxima in the EPR spectra of the two radicals (~230 MHz) is comparable with the nuclear Larmor frequency of the nuclei that are to be polarized ($\omega_n/2\pi = \nu_n$).
Figure 3B:
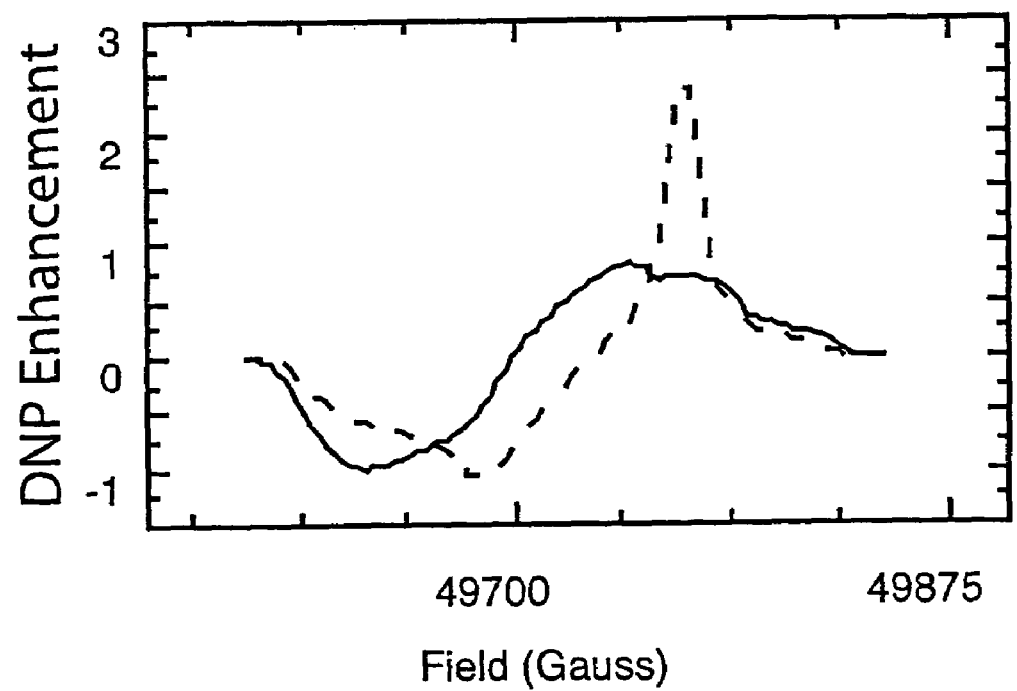
FIG. 3b is a plot of the calculated DNP enhancement as a function of magnetic field. The solid curve is for TEMPO and the dashed curve is for a mixture of TEMPO and trityl.
Figure 3C:
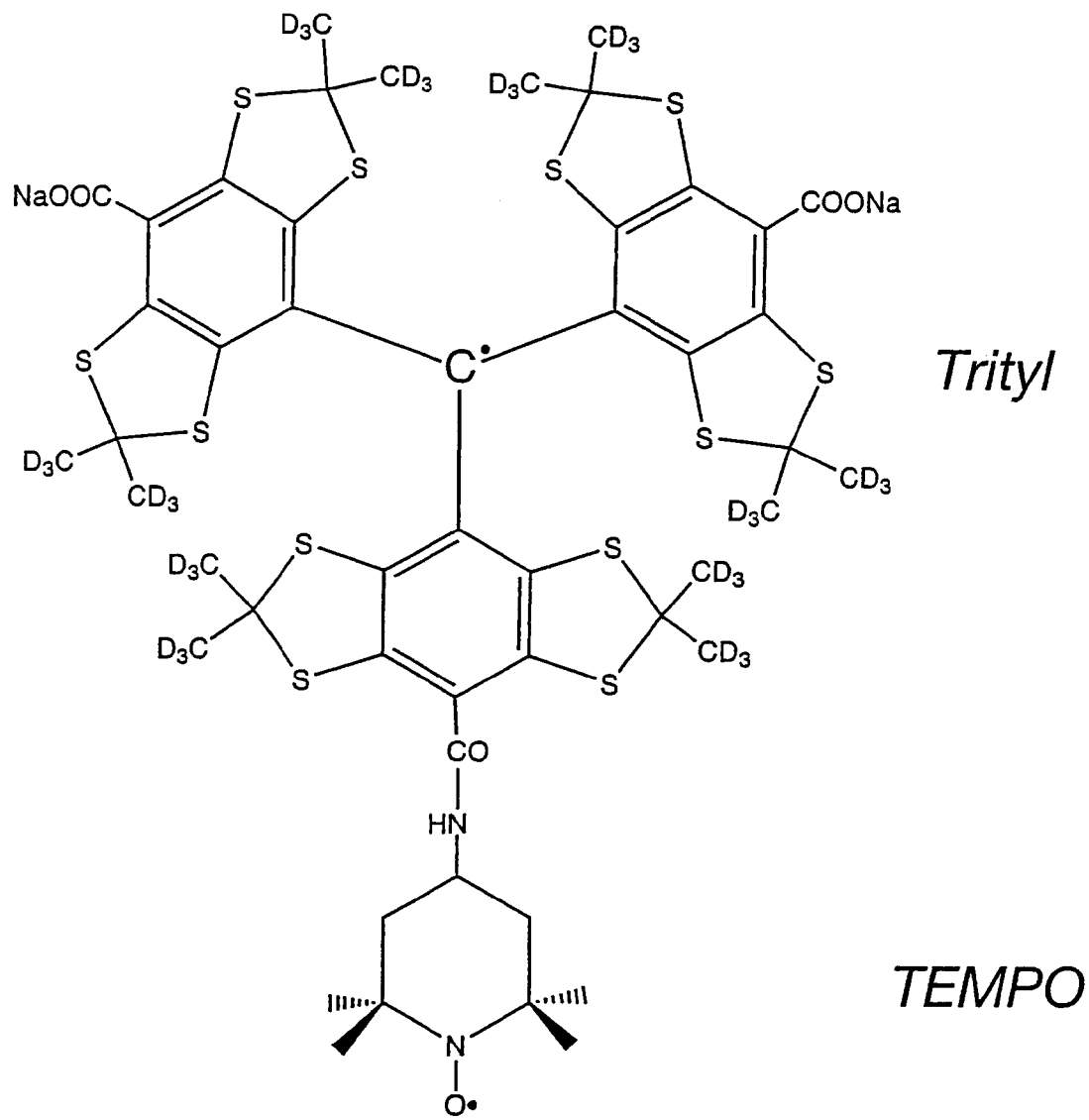
FIG. 3d compares experimental DNP enhancements that were obtained with a mixture of TEMPO and trityl (solid line) and the TEMPO biradical of FIG. 2 (dashed line, n=2). The structure of an exemplary TEMPO-trityl biradical is illustrated in FIG. 3c.

Two different implementations of the present invention are illustrated in FIGS. 2 and 3c. As discussed above, the inventive polarizing agent includes at least two paramagnetic centers. These paramagnetic centers are stable (e.g., in certain embodiments the polarizing agents are ground state triplet states) and hence differ from the paramagnetic centers that are transiently generated in photo-excited triplet states. For a particular polarizing agent to contribute to the DNP enhancement, it will include paramagnetic centers with resonance frequencies that are separated by the nuclear Larmor frequency of the nucleus of interest. It will be appreciated that the required difference in resonance frequency between the paramagnetic centers may result from g-anisotropy and/or differences in the isotropic g-values of the centers. The former situation is illustrated in FIG. 1a (and Example 1) while the latter is illustrated in FIG. 3a (and Examples 2-3).

The situation of FIG. 1a is likely to apply when the polarizing agent includes two paramagnetic centers with very similar or identical isotropic g-values as in FIG. 2 (e.g., the polarizing agent of Example 1 that includes two tethered TEMPO radicals). As shown in FIG. 1a, the electron spins that participate in the dynamic nuclear polarization of the selected nuclei will be separated within the powder averaged spectrum by the nuclear Larmor frequency of the nuclei. In certain embodiments it may prove advantageous to arrange the two radicals within the polarizing agent in such a way that their relative orientations are constrained. Specifically, it is anticipated that certain relative orientations will optimize the DNP enhancement and the optimized orientations are expected to depend on producing the correct relative orientation of the g-tensors of the paramagnetic centers within the polarizing agent.

Figure 3D:
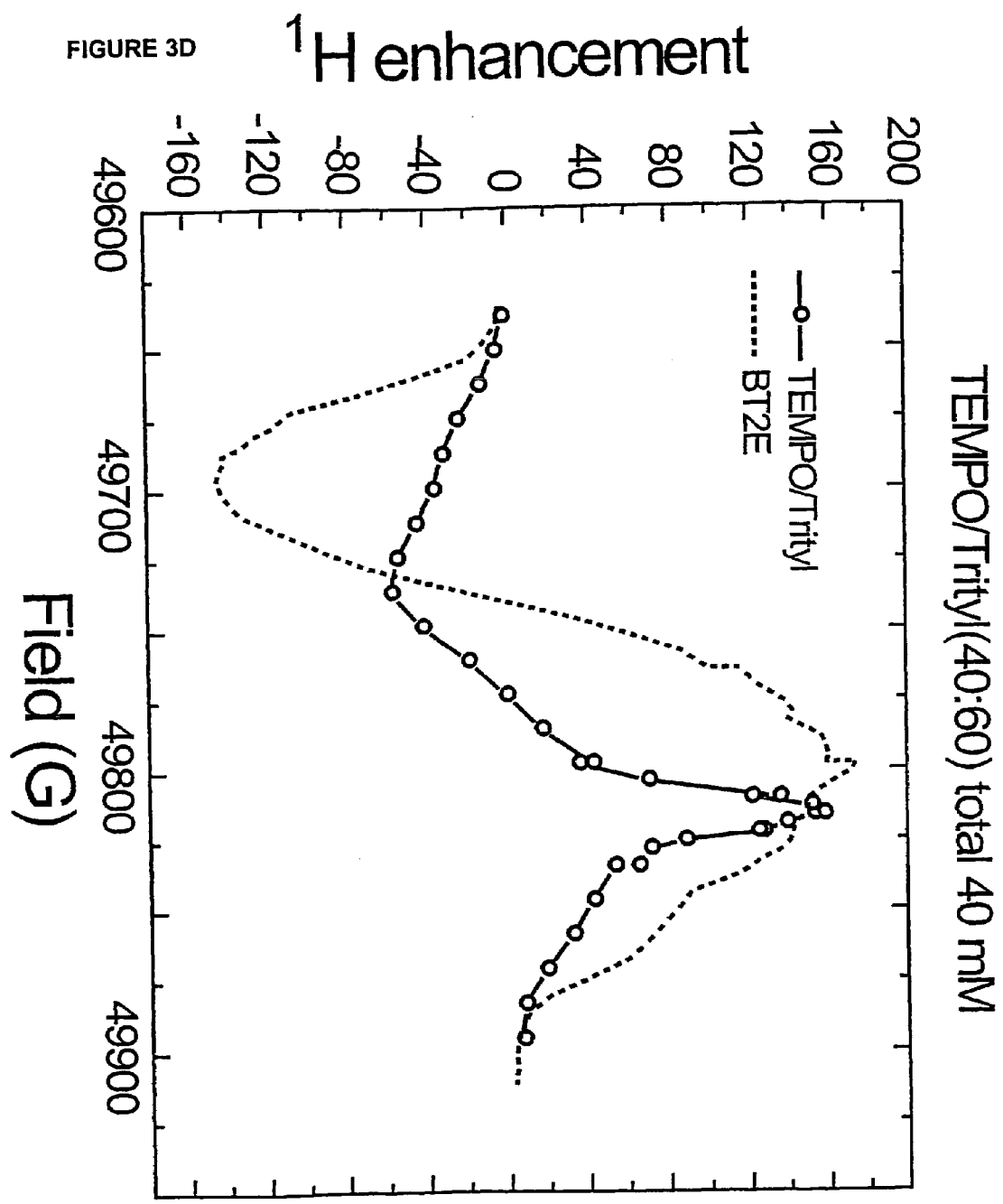

The situation of FIG. 3a is likely to apply when the polarizing agent includes two paramagnetic centers with very different isotropic g-values (e.g., the polarizing agent of FIG. 3c and Example 3 that includes a TEMPO radical tethered to a trityl radical). In the spectrum illustrated in FIG. 3a, the electron spins that participate in the dynamic nuclear polarization of the selected nuclei are again separated by the nuclear Larmor frequency of the nuclei. However, in this case the two electrons are located within two different powder spectra. One of these (dashed line) is due to the trityl radical which has a small g-anisotropy, and the second (solid line) is due to the TEMPO radical which has a large g-anisotropy. It is preferred that the maxima in the these two spectra are separated by the nuclear Larmor frequency of the nuclei since this will ensure that the greatest number of polarizing agents in a given sample will be able to contribute to the DNP. FIG. 3b shows the theoretical DNP enhancement with TEMPO alone (solid line) and with a mixture of TEMPO and trityl (dashed line). FIG. 3d shows experimental DNP enhancements obtained with a mixture of TEMPO and trityl (solid line) and the n=2 TEMPO biradical of FIG. 2 (dashed line). It is to be understood that the present invention is not limited to such a combination and that a polarizing agent may alternatively be prepared that includes two radicals that both have large or small g-anisotropies. The preferred polarizing agent would be comprised of two radicals with small g-anisotropies and isotropic g-values that are separated by the nuclear Larmor frequency of the nuclear spins that are being polarized.

EXAMPLE 1

The synthesis, purification and identification of biradical molecules followed the procedures of Gagnaire, et al., "Regulation by Potassium Ions of Spin Exchange and Dipolar Splitting in Biradical. A Simple Allosteric System," Tetrahedron Letters, 30(47):6507-6510, 1989, the contents of which are incorporated herein by reference. Nitroxide biradicals with different tether lengths (n=2, 3, and 4) were prepared and the DNP enhancement was observed as the electron-electron dipolar interactions were increased (i.e., as n was reduced).

Figure 4:
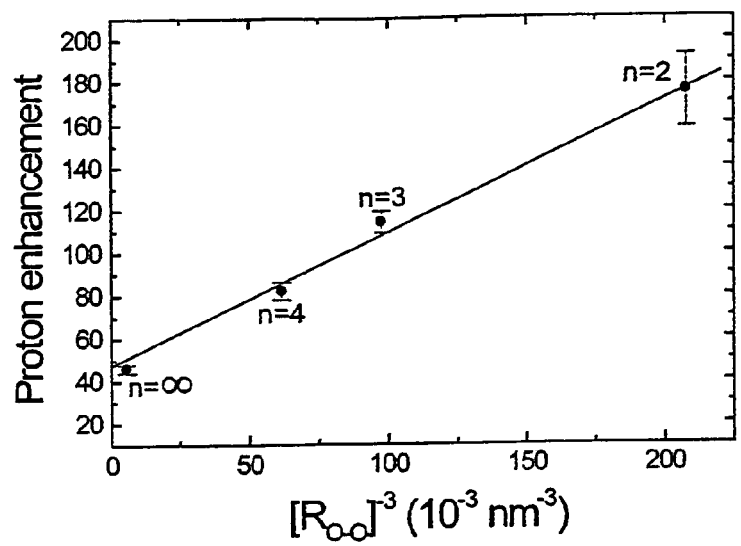
FIG. 4 is a plot of experimental DNP enhancements that were obtained using monomeric TEMPO (n=∞) and the three biradicals of FIG. 2 that are tethered with n=4, 3 and 2 polyethylene glycol units. The DNP enhancements are presented as a function of the approximate electron-electron distance within the polarizing agent, specifically $[R_{O-O}]^{-3}$. Notice that the shorter the linker the larger the enhancement.

The biradical structure was that of a typical oligo-ethylene glycol tethered nitroxide biradical and is illustrated in FIG. 2. The two paramagnetic centers are shown as black dots on the nitroxides at either end of the biradical. The DNP samples using these polarizing agents were dissolved in a mixture of fully deuterated dimethylsulfoxide (d6-DMSO, 99.9%) and partially deuterated water ($D_2O$, 90%) in a weight ratio of 60:40, with 5 mM polarizing agent (10 mM electrons) and 2 M $^{13}C$-urea. The $^1H_2O$ concentration was adjusted to facilitate $^1H$-$^1H$ spin diffusion and subsequent transfer of polarization to the $^{13}C$-urea for measurement of the DNP enhancement. The DNP-NMR experiments were performed on a custom-built DNP-NMR spectrometer, which included a 10 W, 140 GHz gyrotron as a microwave source, a 211 MHz NMR instrument, and a cryogenic Magic Angle Spinning (MAS) probe that can spin a 4 mm sapphire rotor at approximately 3.5 kHz at 90 K. See, Rosay et al., "Two-dimensional $^{13}C$-$^{13}C$ correlation Spectroscopy with Magic Angle Spinning and Dynamic Nuclear Polarization," J. Amer. Chem. Soc., 124(13):3214-3215, 2002, the contents of which are incorporated herein by reference. The proton DNP enhancement was observed indirectly via the cross-polarized $^{13}C$ signal, and its dependence on the size of the electron-electron dipolar interaction $B_{e-e} \sim [R_{o-o}]^{-3}$ is shown in FIG. 4. $R_{O-O}$ is the average electron-electron separation assuming an all-trans polyethylene glycol chain. The experiment of FIG. 4 was performed at 90 K and one can see that the proton DNP enhancement is proportional to the controlled electron-electron dipolar interaction, which goes as $[R^{e-e}]^{-3}$ and is determined by the length of the ($CH_2$—$CH_2$—O) moiety separating the two paramagnetic centers. The point labeled n=∞ in FIG. 4 represents the electron-electron dipolar coupling among evenly distributed monoradicals.

Figure 5:
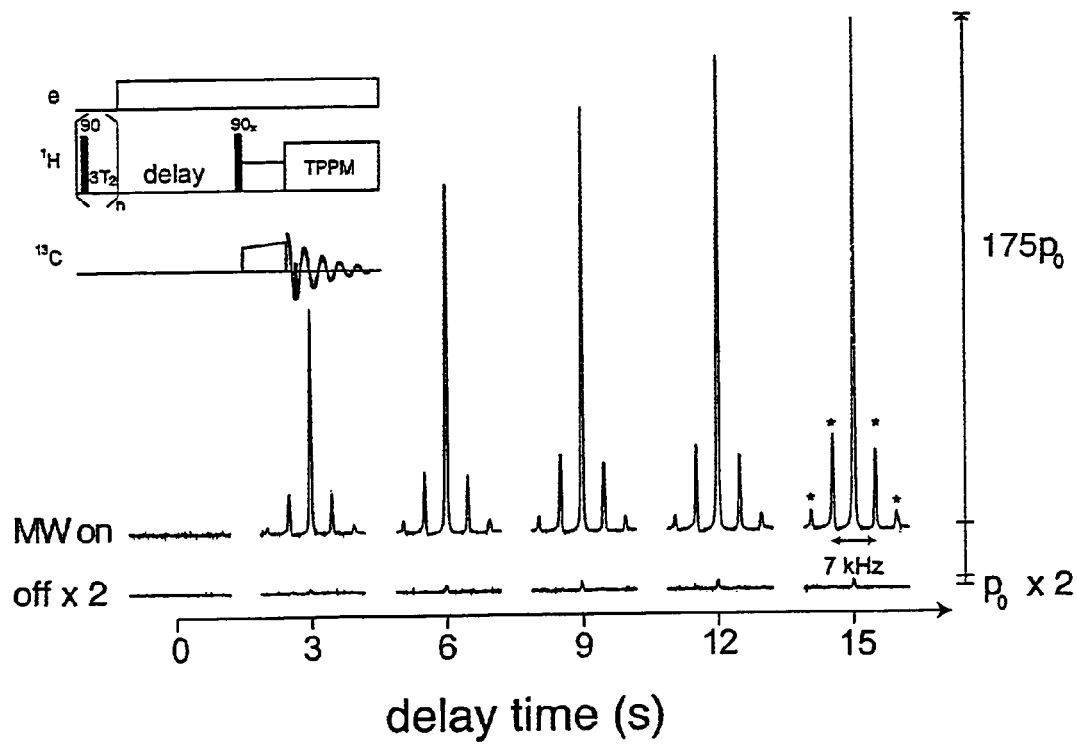

FIG. 5 shows a series of DNP-enhanced spectra of urea obtained using the n=2 biradical with increasing periods of microwave irradiation. The pulse sequence used to record the spectra is shown in the inset of FIG. 5. The lower traces are the spectra obtained without microwave irradiation while the upper traces are the spectra obtained with microwave irradiation. The difference between the upper and lower traces represents the DNP enhancement. As illustrated, an enhancement of 175 was obtained with 12-15 seconds of microwave irradiation. This enhancement is larger by a factor of ~4 than the enhancement observed when monomeric TEMPO is used as a polarizing agent.

EXAMPLE 2

As discussed previously, the DNP enhancement can also be preferably achieved when the EPR spectra of two different paramagnetic centers show maxima in the spectral intensity that are separated by the nuclear Larmor frequency as illustrated in FIGS. 3a-d. This relationship may, for example, be achieved by tethering two different radicals such as a trityl radical and a nitroxide radical as described in the Example 3 below (see FIG. 3c). Indeed, the narrow trityl line and the g22 value of the TEMPO powder pattern are approximately separated by the nuclear Larmor frequency (see FIG. 3a). FIG. 3b shows the predicted DNP enhancements with TEMPO alone (solid line) and with a mixture of TEMPO and trityl (dashed line). The mixture of monoradicals models a TEMPO-trityl biradical with infinite separation. FIG. 3d (solid line) shows experimental results that were obtained with a mixture of TEMPO and trityl (40:60, total concentration 40 mM). As shown in FIG. 3d an enhancement of ~160 was observed with this mixture and is comparable to the enhancement that was obtained with the n=2 TEMPO biradical of FIG. 2 (dashed line). It is anticipated that even larger enhancements will be obtained when the TEMPO and trityl radicals are tethered and the dipolar coupling is thereby increased (e.g., see Example 3).

EXAMPLE 3

A compound having the structure illustrated in FIG. 3c is made via the succinimide ester of trityl and 4-amino-TEMPO. The use of this polarizing agent for DNP studies is performed at cryogenic temperatures as described above in Examples 1 and 2.

EXAMPLE 4

For signal enhancement of magnetic resonance imaging (MRI) studies on organisms (e.g., patients), the polarizing agent of the invention is mixed with an imaging agent. After polarization of a selected nucleus (typically $^{13}C$ or $^{15}N$) within the imaging agent is complete the sample is introduced (e.g., via injection) into the organism under study. If DNP is performed in the solid state the polarized sample is melted or sublimed prior to introduction into the organism. Any imaging agent may be used; however, it is preferred that the polarized nuclei exhibit slow longitudinal relaxation so that polarization is maintained for a sufficient length of time for transfer into an organism and subsequent imaging. Preferred imaging agents include nuclei with longitudinal relaxation time constants ($T_1$) that are greater than 10 seconds, preferably greater than 30 seconds and even more preferably greater than 60 seconds. Without limitation, some exemplary imaging agents that may be used are sodium pyruvate-1-$^{13}C$, acetate-1-$^{13}C$, bicarbonate-$^{13}C$, alanine-1-

$^{13}$C and $^{13}$C-urea. All of these compounds have $^{13}$C longitudinal relaxation times on the order of 30-40 seconds in solution.

It is to be understood that the present invention is not restricted to polarizing agents that include only nitroxide and trityl radicals. Without limitation, other suitable radicals include bis-diphenylene-phenyl-allyl which could be tethered to TEMPO or other radicals. In addition, a variety of biradicals and molecules that include more than two paramagnetic centers have been described and studied in the field of Electron Paramagnetic Resonance (EPR). See, G. Luckhurst "Biradicals as Spin Probes" in *Spin labeling Theory and Applications*, pp. 133-181, L. Berliner Editor, Academic Press (1976). Methods for preparing these are also known. See, Turro et al., "An Electron Spin Polarization Study of the Interaction of Photoexcited Triplet Molecules with Mono-And Polynitroxyl Stable Free Radicals," J. Phys. Chem. 97:1138-1146, 1993. It is contemplated that the polarizing agents of the invention can be used to enhance DNP in solids as well as in solutions. The contents of all of the references included in this specification are incorporated herein by reference.

It is recognized that modifications and variations of the invention disclosed herein will occur to those skilled in the art and it is intended that all such modifications and variations be included within the scope of the appended claims.

What is claimed is:

1. A method comprising steps of:
   placing a sample that includes a polarizing agent within a magnetic field, wherein the polarizing agent is a ground state triplet molecule which comprises two or more unpaired electrons and at least two of the unpaired electrons have spin resonance frequencies that are separated by the spin resonance frequency of a selected nucleus within the sample; and
   irradiating the sample with radiation that causes a mutual electron spin flip of the at least two unpaired electrons in combination with a nuclear spin flip of the selected nucleus so that the nuclear polarization of the selected nucleus is enhanced.

2. The method of claim 1 further comprising detecting the enhanced nuclear polarization by nuclear magnetic resonance.

3. The method of claim 1 further comprising introducing the sample into an organism and detecting the enhanced nuclear polarization by magnetic resonance imaging.

4. The method of claim 1 wherein the polarizing agent comprises two tethered radical molecules.

5. The method of claim 4 wherein the two tethered radical molecules are the same.

6. The method of claim 5 wherein the EPR linewidth of the polarizing agent is greater than the nuclear spin resonance frequency of the selected nucleus.

7. The method of claim 5 wherein the tethered radical molecules are nitroxides.

8. The method of claim 7 wherein the tethered radical molecules are TEMPO linked by polyethylene glycol.

9. The method of claim 4 wherein the two tethered radical molecules are different.

10. The method of claim 9 wherein maxima in spectral intensity of EPR spectra of the two tethered radical molecules are approximately separated by the nuclear spin resonance frequency of the selected nucleus.

11. The method of claim 9 wherein the tethered radical molecules are trityl and nitroxide radicals.

12. The method of claim 2 or 3 wherein the sample further includes an imaging agent and wherein the enhanced nuclear polarization is detected on a nucleus of the imaging agent after the enhanced nuclear polarization has been transferred from the selected nucleus to the nucleus on the imaging agent.

13. The method of claim 12 wherein the enhanced nuclear polarization is detected on a nucleus of the imaging agent with a longitudinal relaxation time constant that is greater than 10 seconds.

14. The method of claim 12 wherein the imaging agent is selected from the group consisting of sodium pyruvate-1-$^{13}$C, acetate-1-$^{13}$C, bicarbonate-$^{13}$C, alanine-1-$^{13}$C and $^{13}$C-urea.

15. The method of claim 1 wherein in the step of irradiating, the sample is at a temperature of less than about 150 K.

16. The method of claim 15 wherein the sample further includes an imaging agent and wherein the enhanced nuclear polarization is detected on a nucleus of the imaging agent after enhanced nuclear polarization has been transferred from the selected nucleus to the nucleus on the imaging agent, the method further comprising melting or subliming the sample and then introducing the sample into an organism.

17. The method of claim 1 wherein the difference in spin resonance frequency of the at least two unpaired electrons results solely from g-anisotropy.

18. The method of claim 1 wherein the difference in spin resonance frequency of the at least two unpaired electrons results from a difference in isotropic g-value.

19. The method of claim 16 wherein the enhanced nuclear polarization is detected on the nucleus of the imaging agent by magnetic resonance imaging.

20. The method of claim 1 wherein the sample includes an amount of non-deuterated wate and the selected nucleus is a proton of the non-deuterated water.

* * * * *